(12) United States Patent
Benharash et al.

(10) Patent No.: US 11,464,894 B2
(45) Date of Patent: Oct. 11, 2022

(54) AUTOMATED OPTICAL DETECTION OF AIR LEAKS IN CHEST TUBE DRAINAGE SYSTEM

(71) Applicant: THE REGENTS OF THE UNIVERSITY OF CALIFORNIA, Oakland, CA (US)

(72) Inventors: Peyman Benharash, Oakland, CA (US); Robert Cameron, Oakland, CA (US); Allen Zhu, Oakland, CA (US)

(73) Assignees: The Regents of the University of California, Oakland, CA (US); Department of Veterans Affairs, Washington, DC (US)

( * ) Notice: Subject to any disclaimer, the term of this patent is extended or adjusted under 35 U.S.C. 154(b) by 392 days.

(21) Appl. No.: 16/320,145

(22) PCT Filed: Jul. 24, 2017

(86) PCT No.: PCT/US2017/043470
§ 371 (c)(1),
(2) Date: Jan. 24, 2019

(87) PCT Pub. No.: WO2018/022489
PCT Pub. Date: Feb. 1, 2018

(65) Prior Publication Data
US 2019/0262515 A1   Aug. 29, 2019

Related U.S. Application Data

(60) Provisional application No. 62/366,369, filed on Jul. 25, 2016.

(51) Int. Cl.
*A61M 1/00* (2006.01)
*A61M 1/04* (2006.01)
(Continued)

(52) U.S. Cl.
CPC ............... *A61M 1/61* (2021.05); *A61M 1/04* (2013.01); *G01M 3/083* (2013.01); *G01M 3/38* (2013.01); *A61B 5/1455* (2013.01); *A61M 1/16* (2013.01); *A61M 2205/15* (2013.01); *A61M 2205/3306* (2013.01)

(58) Field of Classification Search
CPC .. A61M 1/0013; A61M 1/04; A61M 2205/15; A61M 2205/3306; A61M 1/16; G01M 3/083; G01M 3/38; A61B 5/1455
(Continued)

(56) References Cited

U.S. PATENT DOCUMENTS 4,366,384 A * 12/1982 Jensen .................. A61M 5/365
250/575
4,617,020 A * 10/1986 Kurtz .................. A61M 1/0013
600/573
(Continued)

*Primary Examiner* — Andrew J Mensh
(74) *Attorney, Agent, or Firm* — Riverside Law LLP

(57) ABSTRACT

An air leak detection system for chest tube collection systems includes a light emitting element, such as an LED, and a photodetector that can detect reflected light emission generated by the light emitting element. The air leak detection system can include a securement component, such as a transparent clip or adhesive, so that the air leak detection system is compatible with any conventional chest tube collection system. In certain embodiments, the light emitting element is positioned closer to the bottom portion of the water seal tube than the photodetector. In certain embodiments, the photodetector is positioned closer to a bottom of the water seal chamber than the light emitting element. In certain embodiments, the air leak detection system is part of a chest tube drainage system. A method of detecting an air leak in a chest tube collection system is also disclosed.

24 Claims, 15 Drawing Sheets

(51) Int. Cl.
  *G01M 3/08* (2006.01)
  *G01M 3/38* (2006.01)
  *A61M 1/16* (2006.01)
  *A61B 5/1455* (2006.01)

(58) Field of Classification Search
  USPC .......................................................... 604/319
  See application file for complete search history.

(56) References Cited

U.S. PATENT DOCUMENTS

| | | | | |
|---|---|---|---|---|
| 4,650,476 | A * | 3/1987 | Telang | A61M 1/0013 137/205 |
| 4,884,065 | A * | 11/1989 | Crouse | A61M 5/365 340/632 |
| 5,442,435 | A * | 8/1995 | Cooper | G01N 21/43 356/133 |
| 6,529,751 | B1 * | 3/2003 | Van Driel | A61M 1/3626 250/573 |
| 7,726,174 | B2 * | 6/2010 | Riley | G01N 29/222 73/19.03 |
| 2003/0212337 | A1 * | 11/2003 | Sirokman | A61M 1/0013 600/529 |
| 2011/0152642 | A1 * | 6/2011 | Robinson | A61B 5/150236 600/309 |
| 2012/0120384 | A1 * | 5/2012 | Barrett | A61B 5/1455 356/41 |
| 2013/0030405 | A1 * | 1/2013 | Hartman | A61M 5/16831 604/500 |
| 2014/0058274 | A1 * | 2/2014 | Landesberg | A61M 16/0051 600/484 |

* cited by examiner

AUTOMATED OPTICAL DETECTION OF AIR LEAKS IN CHEST TUBE DRAINAGE SYSTEM

CROSS-REFERENCE TO RELATED APPLICATIONS

This application is a national stage filing of International Application No. PCT/US17/43470, filed Jul. 24, 2017, which claims priority to U.S. Provisional Application No. 62/366,369 filed on Jul. 25, 2016, the contents of which are incorporated herein by reference in their entireties.

STATEMENT REGARDING FEDERALLY SPONSORED RESEARCH OR DEVELOPMENT

This work was supported by the U.S. Department of Veterans Affairs, and the Federal Government has certain rights in the invention.

BACKGROUND OF THE INVENTION

Management and monitoring of chest tube drainage systems is a crucial part of the care of many patients with chest diseases and can prove to be challenging. Chest tube drainage systems are routinely used to remove blood, fluid, and air from the pleural space. Air leaks are one of the most prevalent complications related to chest tube use after many common surgical procedures (such as pulmonary resections) and have been associated with increased length of stay and morbidity. Conventional chest tube drainage systems typically have a chest tube that is connected to a collection system which includes a drainage collection chamber, a water seal chamber, and a suction control chamber.

One of the primary functions of the water seal chamber is to visually detect pulmonary air leaks. However, detection of air leaks is completely subjective and is highly variable amongst medical professionals. An experienced surgeon/observer can easily discern air leakage through the chest tube system, and currently, air leaks are typically visually detected by a trained observer, such as a surgeon. However, such highly trained individuals are available to monitor air leakage for only a few minutes each day. Furthermore, there are few other qualified hospital personnel outside of thoracic specialists trained to reliably detect and manage ongoing or changing air leaks. The lack of knowledge as to variations and changes in air leakage and the uncertainty as to resolution of these leaks leads to longer hospitalization than often necessary, since a "wrong" decision or judgment can lead to life-threatening consequences. Recently, systems such as the collection system marketed under the tradename Thopaz (Medela Inc., McHenry, Ill., USA) have been introduced that consist of a drainage system used to remove air and liquids, similar to common chest tubes. They have the additional feature of air flow and pressure detectors to provide clinicians with information regarding the presence and extent of air leakage, and claim the ability to indicate the presence of a pneumothorax inside the chest. Such devices are also designed to alert hospital staff in a rare case of a needed intervention. These devices are dedicated systems, and require the purchase of a completely new electronic drainage and monitoring system, which further requires a significant commitment to personnel training.

In addition, when a patient takes a deep breath followed by exhalation, an oscillation occurs at the water level within the water seal chamber. This oscillation corresponds to back and forth displacement of air without actually having a leak or bubble. Conventional in-line flow meters suffer from the inability to discriminate between detecting these oscillations versus detecting bubbles.

What is needed in the art is a device and method for automatically and objectively detecting air leaks in a chest tube drainage system. Further, what is needed is a device and method that is compatible with a variety of conventional chest tube drainage systems as an "add on" component. Finally, what is needed in a device and method for monitoring the water seal chamber that can discriminate between detecting oscillations versus detecting bubbles.

SUMMARY OF THE INVENTION

In one embodiment, a chest tube drainage system includes a chest tube collection system including a drainage collection chamber, a water seal chamber, a suction control chamber, and a water seal tube in fluid communication with the drainage collection chamber and the water seal chamber; and an air leak detection system including a light emitting element and a photodetector disposed near a bottom portion of the water seal tube so that the photodetector can detect reflected light emission generated by the light emitting element. In one embodiment, the reflected light emission is reflected off of a fluid in the water seal chamber. In one embodiment, the reflected light emission is reflected off of one or more bubbles in the water seal chamber. In one embodiment, the light emitting element is an LED. In one embodiment, the light emitting element is disposed closer to the bottom portion of the water seal tube than the photodetector. In one embodiment, the photodetector is disposed closer to a bottom of the water seal chamber than the light emitting element. In one embodiment, multiple photodetectors are deployed and some are used to subtract background noise. In one embodiment, the light emitting element and the photodetector are disposed on a securement device that is configured to attach to the chest tube collection system. In one embodiment, the securement device includes at least one of a clip and an adhesive. In one embodiment, the securement device is transparent. In one embodiment, the air leak detection system is configured to perform a fast fourier transform on the detected signal from the photodetector for determining when there is an air leak. In one embodiment, the air leak detection system includes high and low bandpass filters to pass frequencies of 20-30 HZ and 70-90 Hz.

In one embodiment, an air leak detection system includes a light emitting element and a photodetector disposed on a securement device configured to attach to a chest tube collection system; wherein the photodetector is configured to detect light emission reflected off of bubbles within the chest tube collection system. In one embodiment, the securement device is transparent. In one embodiment, the securement device includes at least one of an adhesive and a clip. In one embodiment, the light emitting element is an LED. In one embodiment, the light emitting element and the photodetector are disposed on the securement device so that when the securement device is attached to a chest tube collection system, the light emitting element is positioned closer to the bottom portion of the water seal tube than the photodetector. In one embodiment, the light emitting element and the photodetector are disposed on the securement device so that when the securement device is attached to a chest tube collection system, the photodetector is positioned closer to a bottom of the water seal chamber than the light emitting element. In one embodiment, the air leak detection system includes high and low bandpass filters to pass frequencies of 20-30 HZ and 70-90 Hz. In one embodiment, the air leak detection system includes an alert module configured to send a signal when a plurality of detected bubble events corresponding to the detected light emission reaches a threshold.

In one embodiment, a method of detecting an air leak in a chest tube collection system includes positioning a light emitting element and a photodetector near a bottom portion of a water seal tube, the water seal tube positioned within a water seal chamber of the chest tube collection system; emitting light from the light emitting element towards bubbles generated by air leaving the water seal tube; and detecting a reflection of the light using the photodetector. In one embodiment, the method includes the step of positioning the light emitting element closer to the bottom portion of the water seal tube than the photodetector. In one embodiment, the method includes the step of positioning the photodetector closer to a bottom of the water seal chamber than the light emitting element. In one embodiment, the method includes the step of detecting a bubble event corresponding to a threshold frequency rise in the 20-30 HZ and 70-90 Hz ranges. In one embodiment, the method includes the step of detecting a plurality of bubble events. In one embodiment, the method includes the step of signaling an alert when the plurality of bubble events reaches a threshold.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 3A is a spring-loaded clip according to one embodiment. FIG. 3B is a slide-on clip according to one embodiment.

FIGS. 9A and 9B are front views of the clip attached to the chest drainage system. FIG. 9C is a back view of the clip arm, and FIG. 9D is a side view of the clip attached to the chest drainage system.

DETAILED DESCRIPTION OF THE INVENTION

Figure 1A:
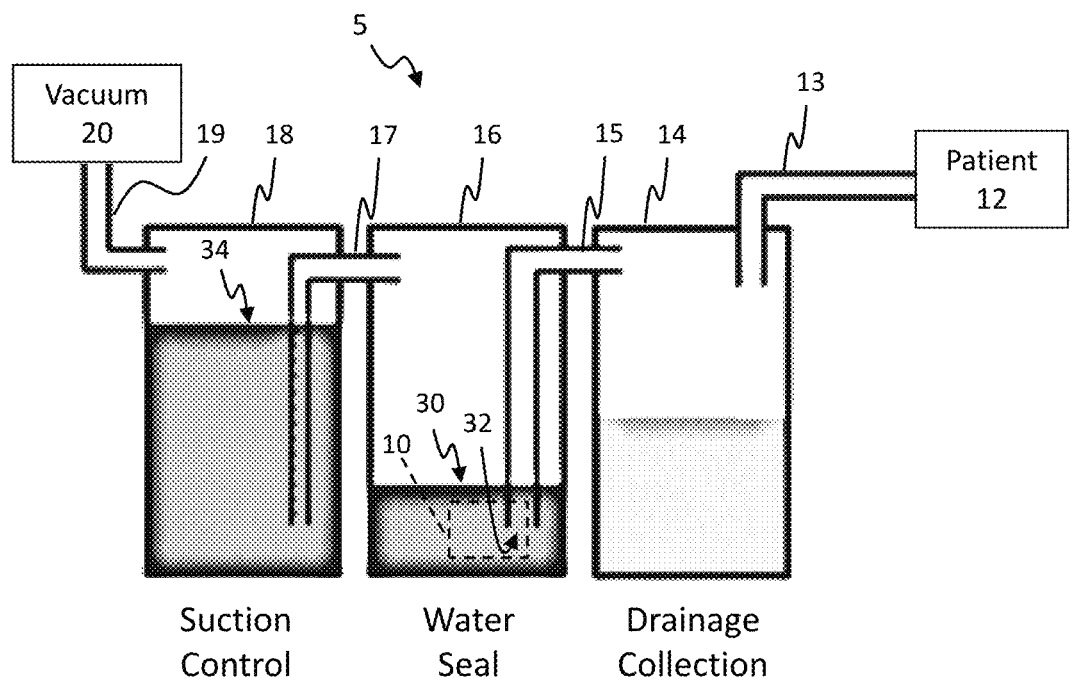
FIG. 1A is a diagram of a chest tube drainage system and FIG. 1B is a diagram of an air leak detection system having a phototransistor and an LED according to an exemplary embodiment.

It is to be understood that the figures and descriptions of the present invention have been simplified to illustrate elements that are relevant for a more clear comprehension of the present invention, while eliminating, for the purpose of clarity, many other elements found in systems and methods of optically detecting air leaks in a chest tube drainage system. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"LED" as used herein refers to light emitting diode.

"ROC" as used herein refers to receiver operating characteristic.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are devices, systems and methods for optically detecting air leaks in a chest tube drainage system.

Figure 1B:
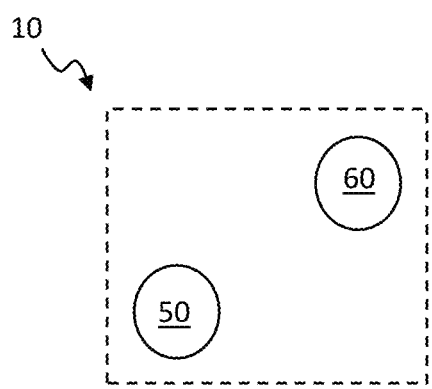
Figure 2:
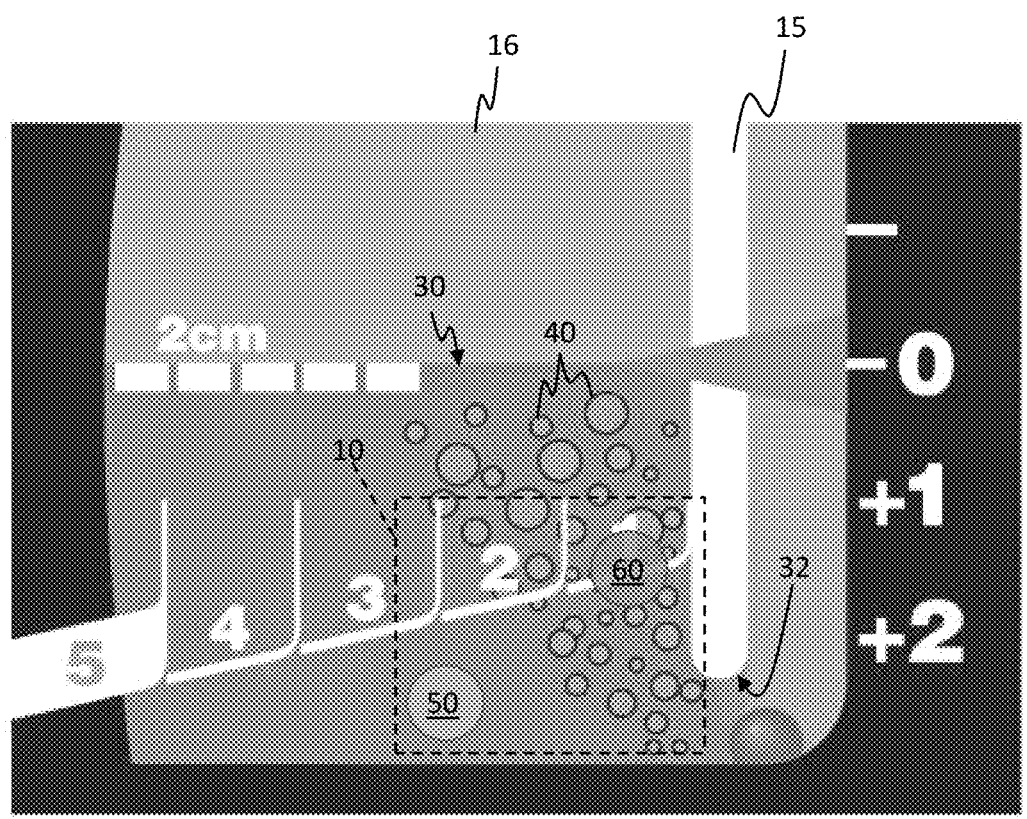
FIG. 2 is a magnified view of a water seal chamber, showing placement of a photodetector and an LED according to an exemplary embodiment.

In one embodiment, a chest tube drainage system includes a chest tube collection system including a drainage collection chamber, a water seal chamber, a suction control chamber, and a water seal tube in fluid communication with the drainage collection chamber and the water seal chamber. An air leak detection system includes a light emitting element and a photodetector disposed near a bottom portion of the water seal tube so that the photodetector can detect reflected light emission generated by the light emitting element. With reference now to FIGS. 1A, 1B and 2, in one embodiment, a chest tube drainage system 5 includes a drainage collection chamber 14 that is connected to a chest tube 13 in fluid communication with the patient's 12 pleural cavity. Blood and fluid from the patient collects in the drainage collection chamber 14. The drainage collection chamber 14 can include multiple compartments in fluid communication with each other, such as a first, second and third compartment for collecting fluid from the patient 12. The water seal chamber 16 is connected to the drainage collection chamber 14 by a water seal chamber tube 15. The bottom portion 32 of the water seal chamber tube 15 is below the water level of the water seal 30. When air moves down the water seal chamber tube 15, it bubbles out and moves into the suction control chamber 18 via the suction control tube 17. The suction control chamber 18 controls the amount of suction the patient gets based on the amount of water 34 in the suction control chamber. A vacuum tube 19 connects the suction control chamber 18 to a vacuum source 20. An air leak detection system 10 is used in conjunction with the chest tube drainage system 5 for detecting air leaks in the chest tube drainage system 5.

In certain embodiments, the light emitting element emits electromagnetic radiation in the visible light spectrum and in certain embodiments, the light emitting element emits electromagnetic radiation at wavelength that is not visible. In certain embodiments, the light emitting element emits electromagnetic radiation in an ultraviolet or an infrared wavelength. In one embodiment, the air leak detection system 10 includes an LED 60 and a photodetector 50 secured to a transparent housing of the water seal chamber 16. In one embodiment, the LED 60 and photodetector 50 are positioned near the bottom 32 of the water seal chamber tube 15. In one embodiment, the LED 60 is adjacent to the bottom 32 of the water seal chamber tube 15, and the photodetector 50 is positioned lower and spaced further away from the water seal chamber tube 15 than the LED 60. In certain embodiments, the LED and photodetector are spaced about 2 cm apart. In certain embodiments, the LED and photodetector are spaced between 0.5 cm and 3 cm apart. In certain embodiments, the water seal chamber 16 housing is transparent and the air leak detection system 10 is secured to the outside of the water seal chamber 16, so that light emitted by the LED 60 is reflected from the fluid in the water seal chamber 16, and detected by the photodetector. In certain embodiments, the LED and photodetector are positioned on the same surface of the water seal chamber housing. In certain embodiments, the LED and photodetector are positioned on adjacent sides or opposite transparent sides of the water seal chamber housing. When the LED and photodetector are positioned on opposing sides of the water seal chamber housing, according to one embodiment, the LED and photodetector are aligned so that interruption or refraction of detected light is indicative of bubbles in the water seal. In one embodiment, the light emitting element is disposed closer to the bottom portion of the water seal tube than the photodetector. In one embodiment, the photodetector is disposed closer to a bottom of the water seal chamber than the light emitting element. When air goes through the water seal chamber 16, the bubbles that rise diffract the emitted light from the LED 60, generating a signal in the photodetector 50. The placement of the air leak detection system 10 can be on the transparent area on the water seal chamber 16 that is normally used clinically to visibly detect air leaks. In certain embodiments, one or both of the LED and photodetector are water resistant, and are placed inside the water seal chamber 16 in contact with fluid. The LED can be substituted for another suitable light emitting element in the air leak detection system.

Figure 3A:
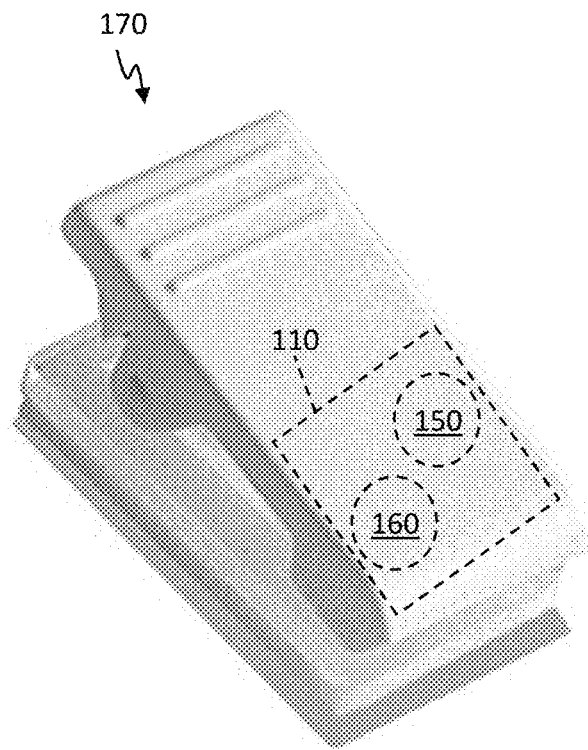
FIGS. 3A and 3B are embodiments of a transparent clip for securing the photodetector and the LED air leak detection system onto an off the shelf chest tube collection system.
Figure 3B:
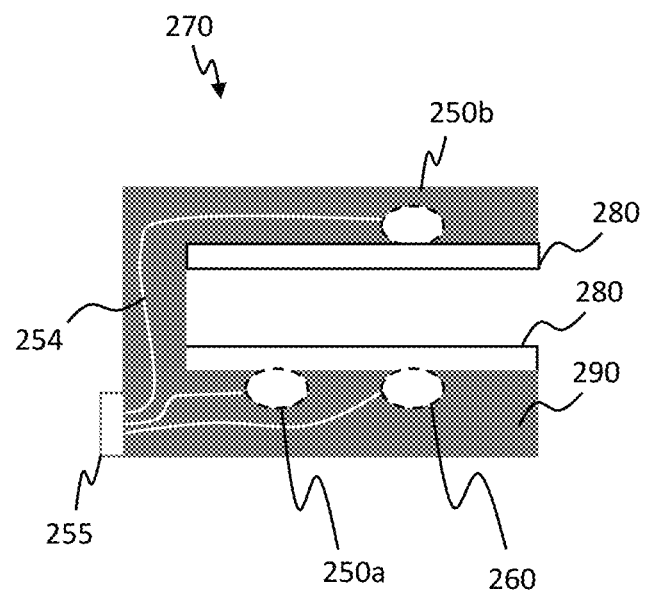

In one embodiment, the air leak detection system 10 is integrated into a clip 70 that attaches to a conventional off the shelf chest tube collection system as shown in FIGS. 3A and 3B. In certain embodiments, the LED and photodetector are housed behind a transparent housing of the clip to allow light to pass through for transmission and detection. As shown in FIG. 3A, in one embodiment, the clip 170 is a spring tension clip that in certain embodiments includes an entirely transparent plastic housing. The air leak detection system 110 includes a LED 160 and a photodetector 150 housed in a same arm of the clip, so that when the clip attaches to the window of the chamber housing, the LED 160 and photodetector 150 are positioned at the proper and desired distance of separation (for example, as shown in FIG. 2). In certain embodiments, both of the LED and photodetector are disposed on the same arm of the clip. In certain embodiments, the LED and photodetector are disposed on opposite arms of the clip so that they align in an opposing configuration once the clip is secured onto the chamber housing. A slide-on clip 270 is shown in FIG. 3B, according to one embodiment. The housing 290 is a plastic with certain portions being a transparent plastic 280 to allow for transmission of light. In certain embodiments, such as the embodiment shown in FIG. 3B, first and second photodetectors 250a and 250b are positioned on each arm of the clip for both same side and opposite side light detection modes, which in certain embodiments can run simultaneously for bubble detection. The same simultaneous detection mode can be accomplished in an alternative embodiment by replacing photodetector 250b with an LED positioned across from 250a. Wires 254 can connect to the system elements to an integrated control module 255 or a wired or wireless communication module that connects to a remote control module. User feedback such as light and audio elements can be connected to the control module to relay the status of the chamber to medical professionals. In one embodiment, an LED 260 and a single photodetector 250a are positioned on the same arm of the clip. In one embodiment, an LED 260 and a single photodetector 250b are positioned in opposing arms of the clip 270. In an alternative embodiment, as would be understood by those having ordinary skill in the art, various combinations of emitters and detectors can be implemented for both same side and opposite side detection. Securement mechanisms for the air leak detection system can include one or more of a clip and an adhesive. Alternatively, the device can be any other removably engageable mechanism capable of securing the device to a chest drainage system.

The refractive properties of bubbles within the water seal chamber are utilized to the advantage of the system, and a phototransistor captures changes in reflected light. In one embodiment, a method of detecting an air leak in a chest tube collection system includes positioning a light emitting element and a photodetector near a bottom portion of a water seal tube, the water seal tube positioned within a water seal chamber of the chest tube collection system; emitting light from the light emitting element towards bubbles generated by air leaving the water seal tube; and detecting a reflection of the light using the photodetector. In one embodiment, the method includes the step of positioning the light emitting element closer to the bottom portion of the water seal tube than the photodetector. In one embodiment, the method includes the step of positioning the photodetector closer to a bottom of the water seal chamber than the light emitting element. In one embodiment, the method includes the step of detecting a bubble event corresponding to a threshold frequency rise in the 20-30 HZ and 70-90 Hz ranges. In one embodiment, the method includes the step of detecting a plurality of bubble events. In one embodiment, the method includes the step of signaling an alert when the plurality of bubble events reaches a threshold. In one embodiment, multiple photodetectors are deployed and some are used to subtract background noise.

Figure 4:
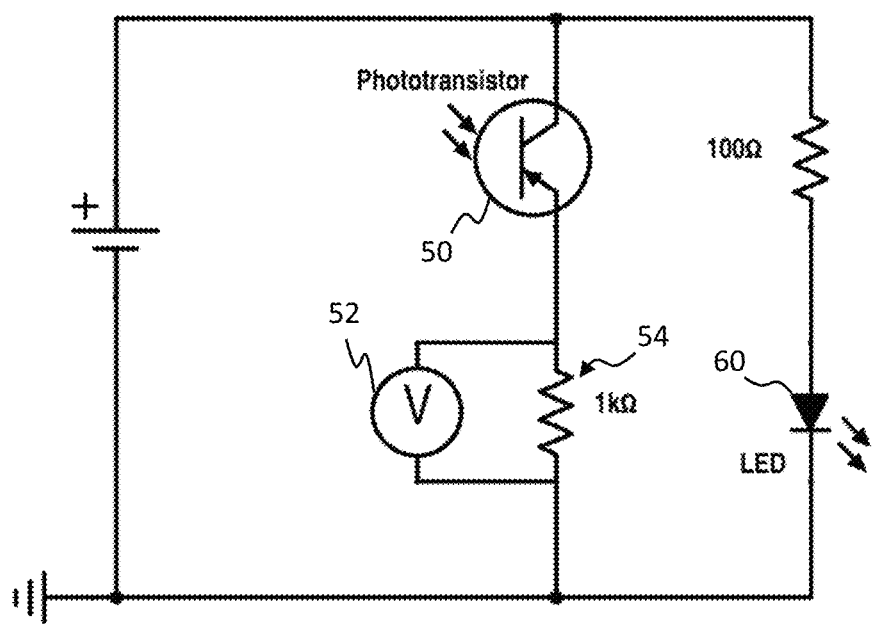
FIG. 4 is a circuit diagram of the phototransistor and LED circuit according to an exemplary embodiment.
Figure 5A:
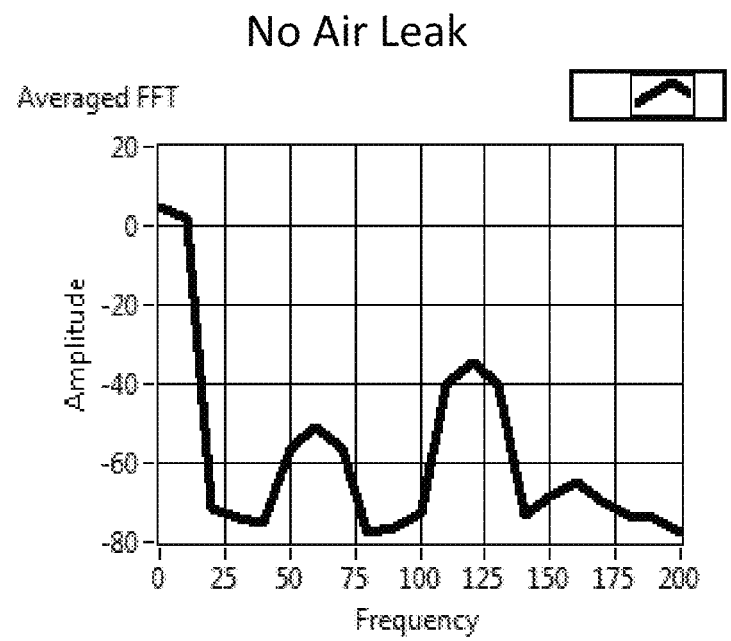
FIGS. 5A and 5B are graphs of the fast fourier transform of the signal from the phototransistor during "no air leak" and "air leak" states respectively according to one example.
Figure 5B:
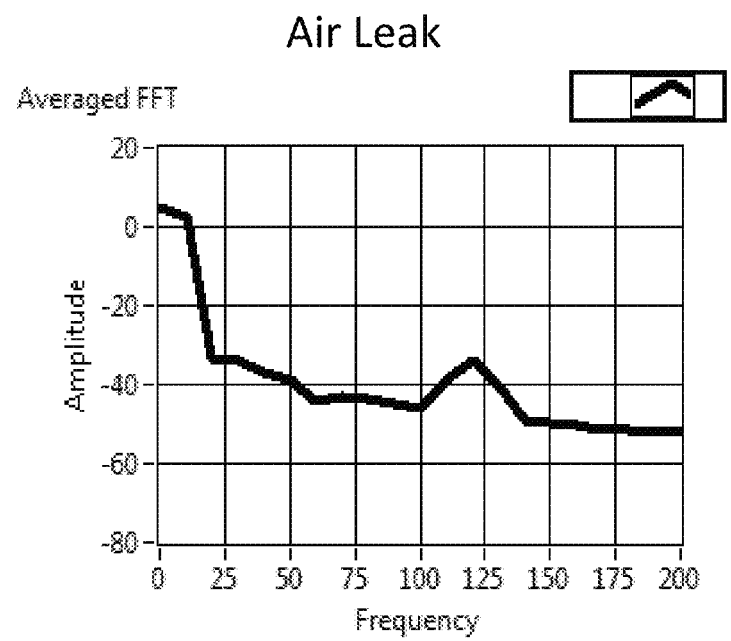
Figure 6A:
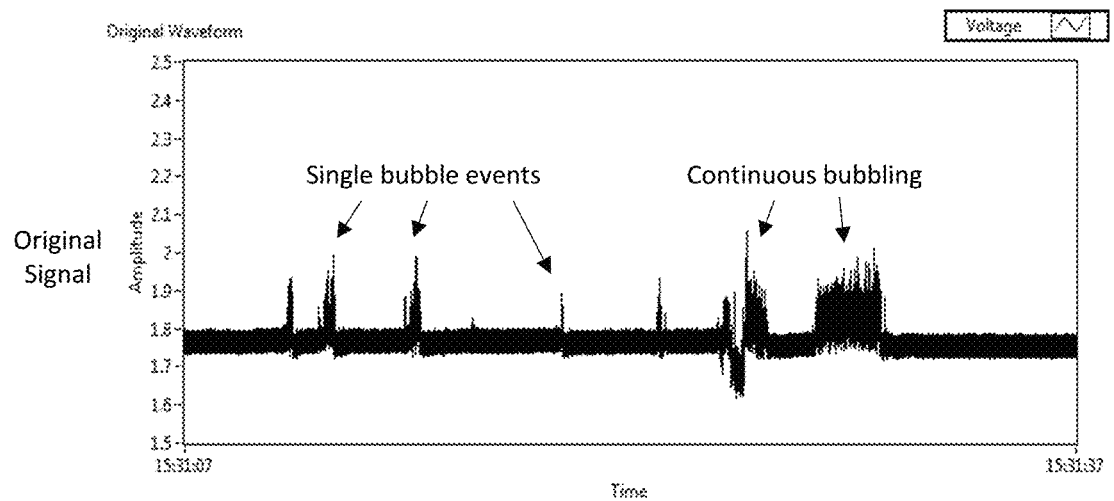
FIGS. 6A-6C are graphs of the raw signal received from the photoresistor (FIG. 6A), after the low bandpass filter is applied (FIG. 6B) and after the high bandpass filters is applied (FIG. 6C) according to one example.
Figure 6B:
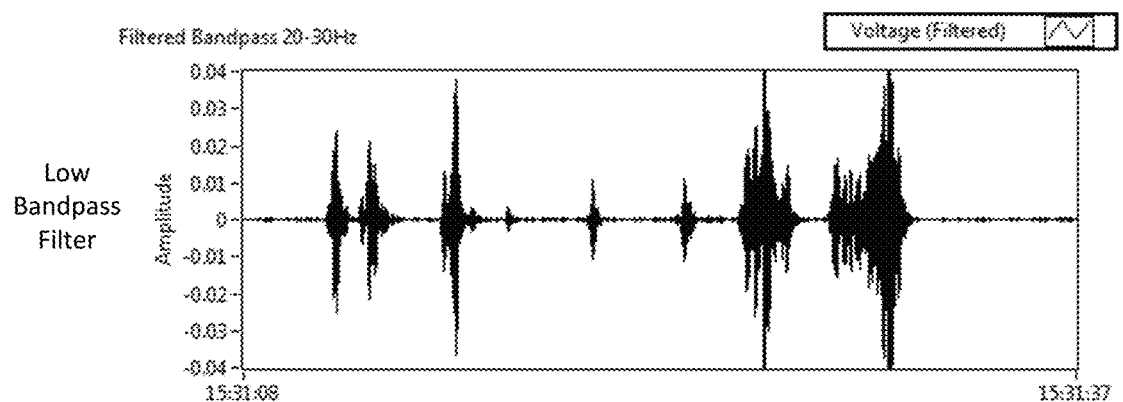
Figure 6C:
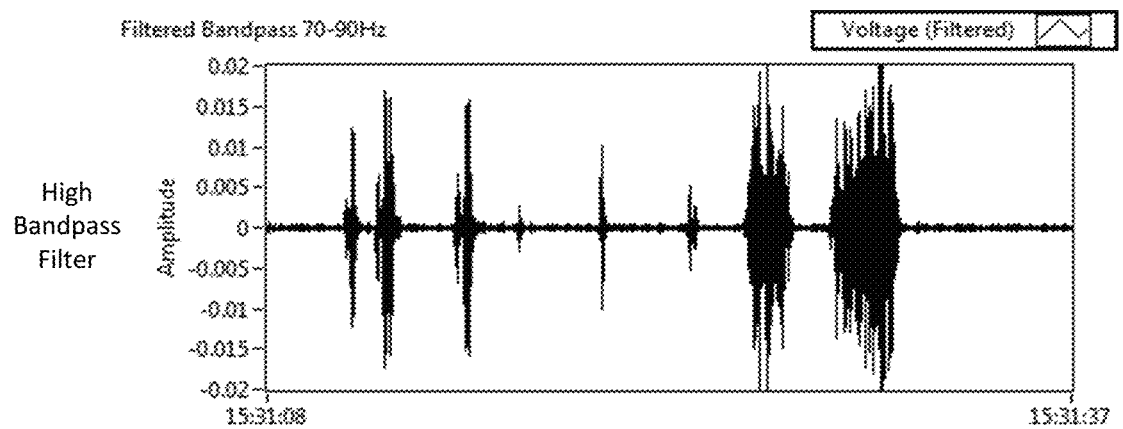
Figure 7A:
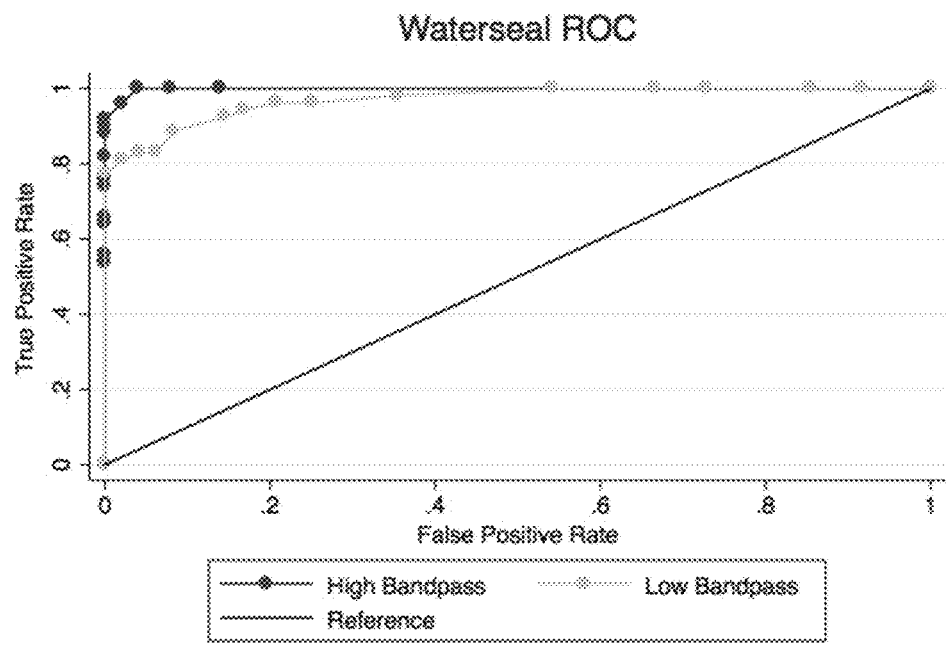
FIGS. 7A and 7B are graphs showing the Receiver Operating Characteristic analysis of the low and high bandpass filters with the chest tube on water seal (FIG. 7A) and the analysis of the low and high bandpass filters with the chest tube on suction (FIG. 7B) according to one example.
Figure 7B:
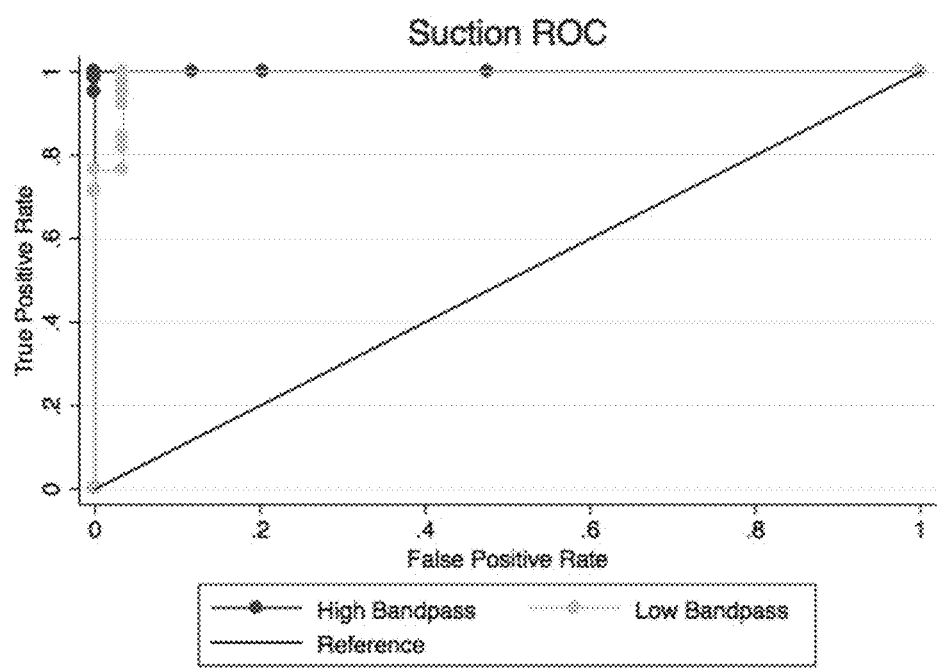

The signal detected by the photodetector can be processed through a software program. The software can be embedded on a portable device, or the photodetector and components of the system can communicate with software run on a remote computer through a wired or a wireless connection. In one embodiment, the software is embedded to make the system completely portable, such as an embodiment on a clip. In one embodiment, as shown in FIG. 4, voltage change was sensed through a resistor 54 and sampled at 1 KHz with an analog-to-digital converter. The voltmeter 52 reads the signal across the resistor 54. Software conducts frequency domain analysis in order to locate optimal regions (high frequency and low frequency) for sensing bubbles. In certain embodiments, digital bandpass filters are applied to these regions and receiver operator curves are generated. In one embodiment, digital signal processing is done using real-time Fourier transformation. As shown in FIGS. 5A and 5B, most frequencies rise when an air leak is present, but some regions have a greater change than others. In one embodiment, bandpass filtering allows two distinct regions, 20-30 HZ and 70-90 Hz, to be used by the algorithm. A dynamic or threshold is selected, and if the signal is higher than the threshold, an event will be registered. In certain embodiments, the threshold is set to a level of around 5 times greater than baseline noise level. As shown in FIGS. 6A-6C, the majority of the noise coming from the raw signal is removed in the filtered waveforms and resulting in a much larger and visible spike when bubbling occurs. With reference to FIGS. 7A and 7B, ROC analysis was performed on the low and high bandpass filters with the chest tube on water seal. Bubbles were generated by blowing into the chest tube. For the high bandpass, the c-statistic=0.998, and for the low bandpass, the c-statistic=0.970. ROC analysis was performed on the low and high bandpass filters with the chest tube on suction. Bubbles were generated by suction. For the high bandpass, the c-statistic=1.00, and for the low bandpass, the c-statistic=0.992.

Advantageously, embodiments of the device described herein are not sensitive to oscillation within the water seal chamber and the detection system only detects actual bubbles passing through the window. Since embodiments of the detector are based on change of refraction index and therefore change in reflection of light when a bubble goes through, the system is much more specific for detecting an actual air leak rather than mere fluctuations in water levels. Conventional in-line flow meters suffer from the inability to discriminate against these oscillations.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Through experimentation, it was demonstrated that the system is successful and accurate at being able to detect bubbles and air leaks within a chest tube drainage system. It has high predictive power under both the high and low bandpass filters. In certain instances, the high bandpass filter performed marginally better. Because the system exhibits excellent discriminant power and can automatically and objectively detect air leaks in clinic, its use could potentially result in decreased length of stay, lowered costs of care, and superior health outcomes for the patient.

In one embodiment, a bubble event registration system records the number of events per time period. For example, in certain embodiments, the computer system generates a time log of bubbles over the desired period of time that may be incorporated into clinical electronic health information systems to provide the surgeons/physicians with 24 hr monitoring of air bubbles. An alarm system to alert hospital staff in the case of irregular behavior also can be included. In certain embodiments, any deviation or change >50% from behavior observed in the previous 30 minute epoch is indicative of irregular behavior.

Figure 8A:
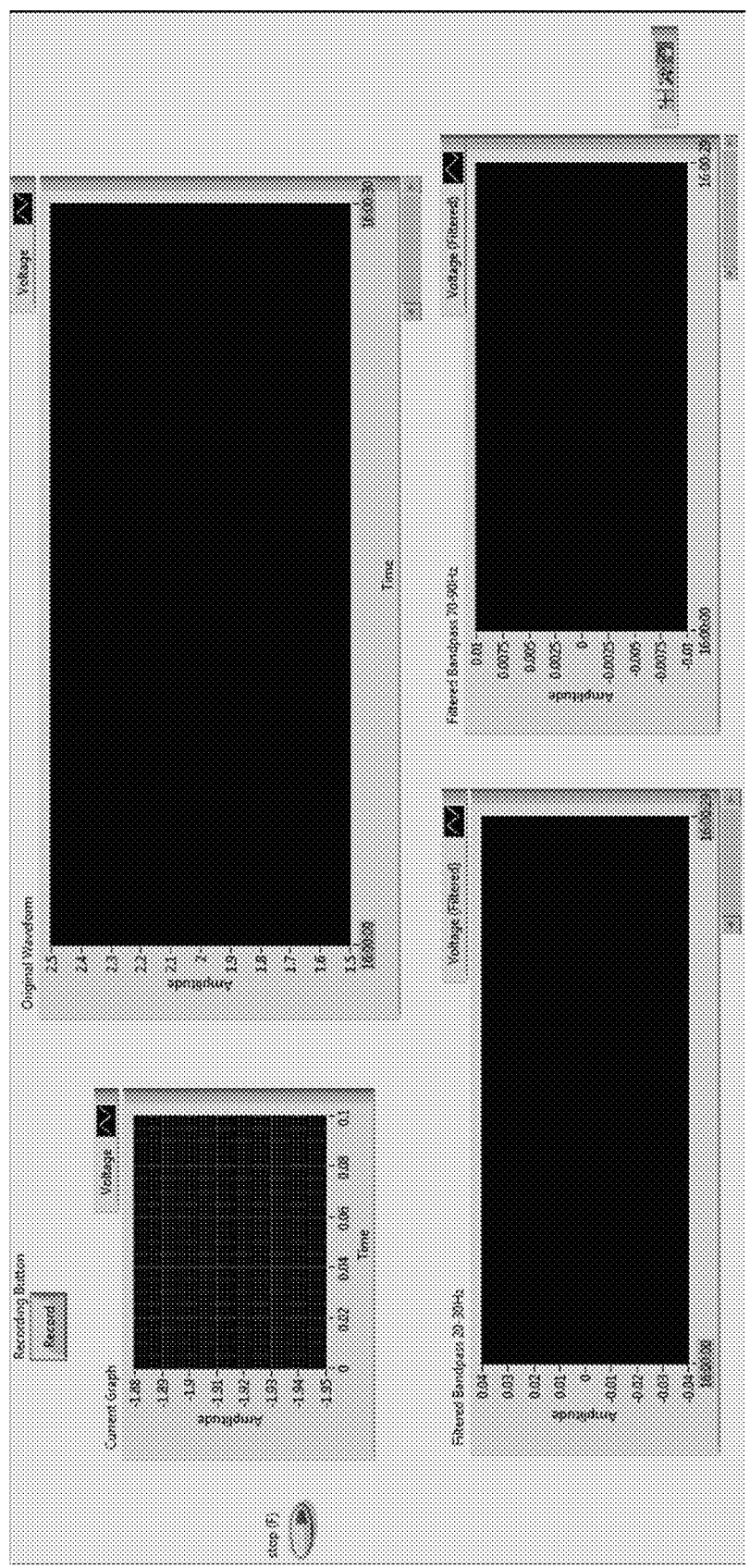
FIGS. 8A and 8B are partial views of a graphical user interface and FIGS. 8C and 8D are partial views of a program flow of software that can be used to monitor the chest tube drainage system.
Figure 8B:
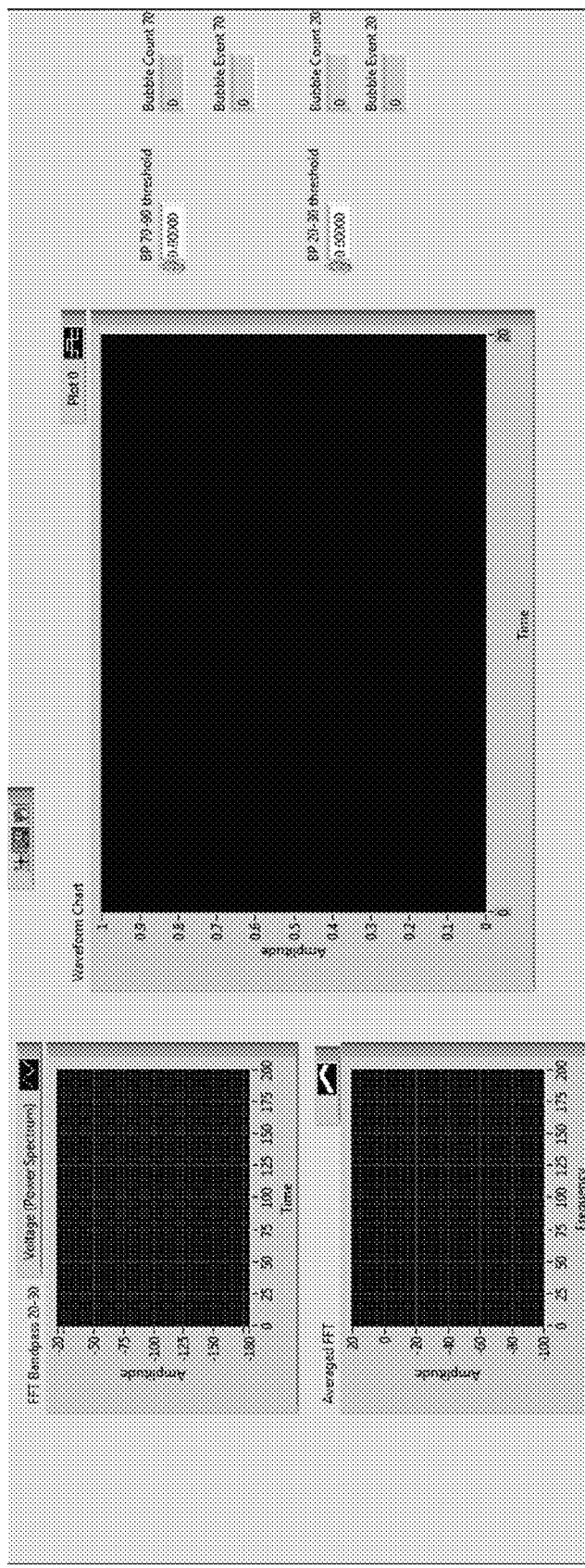
Figure 8C:
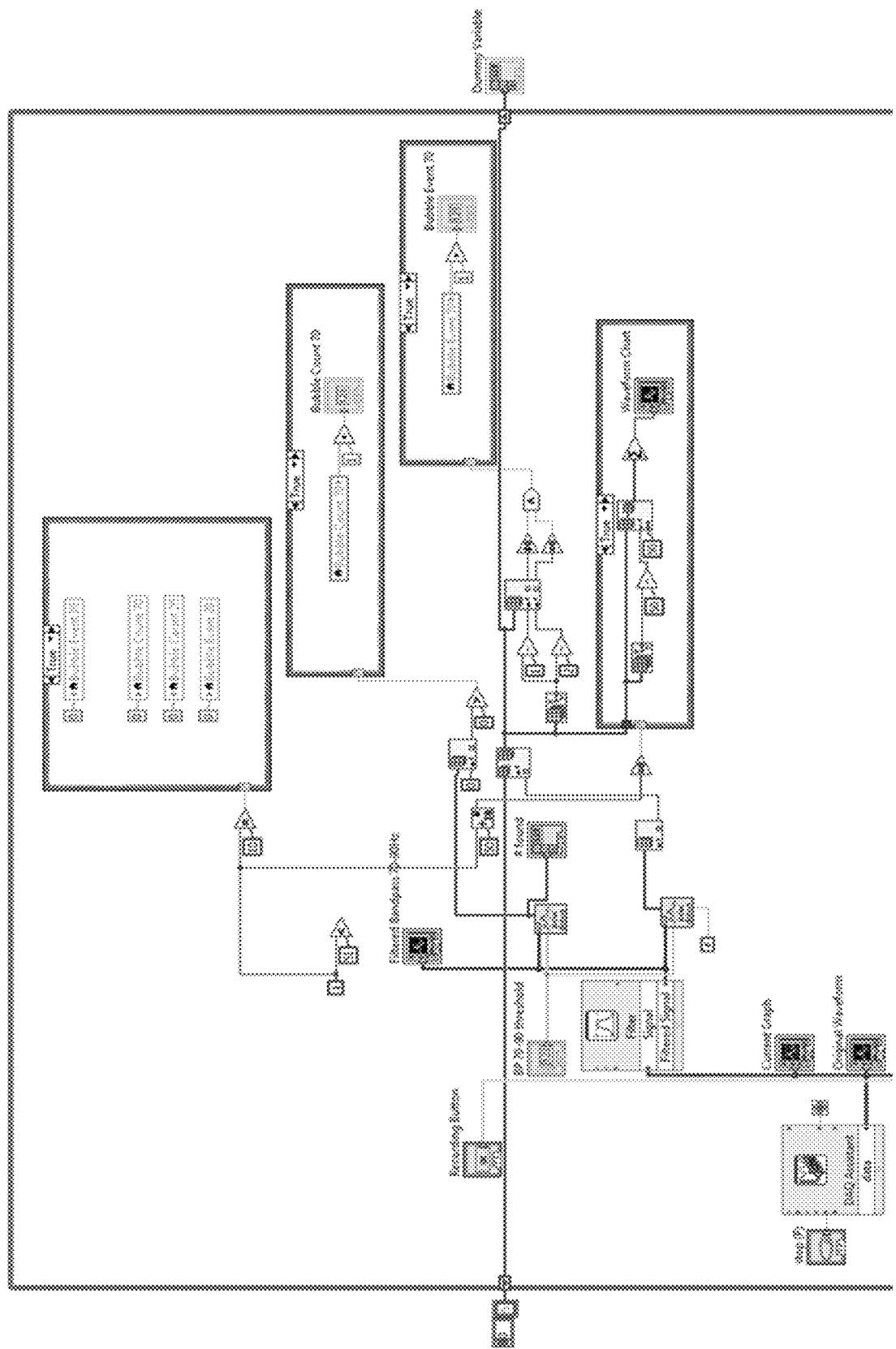
Figure 8D:
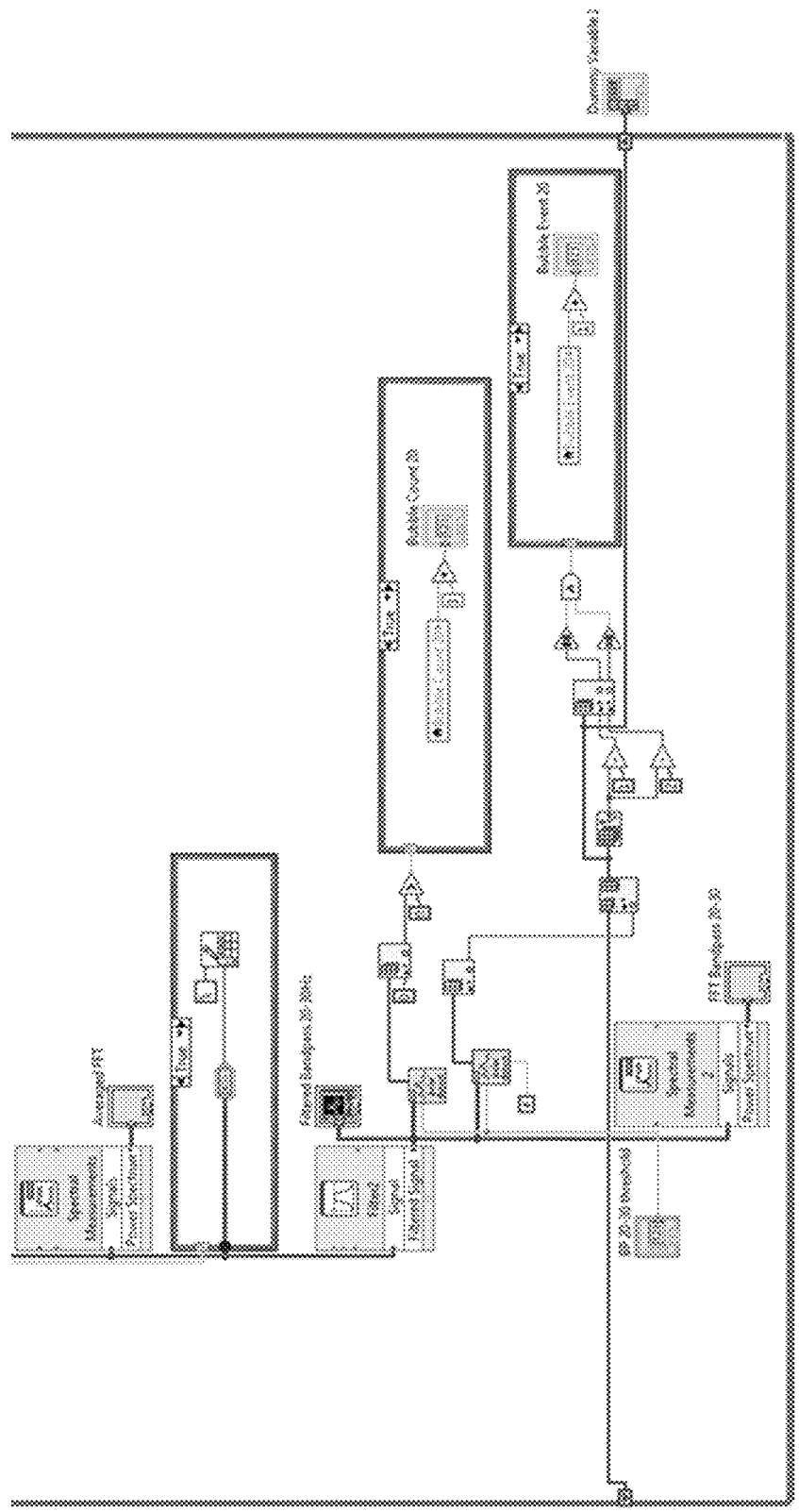

Software can be developed in software suites such as Labview to processes the signal received by the photodetector and display bubble detection information in a guided-user interface, such as the graphical use interface shown in FIGS. 8A and 8B. In certain embodiments, the incoming signal is digitally filtered, either through a 20-30 Hz bandpass filter or a 70-90 Hz bandpass filter. An exemplary back panel of Labview is shown in FIGS. 8C and 8D. The program then performs peak detection on the filtered waveforms for bubble detection. The threshold for peak detection can be changed on the user interface or in the back panel of the Labview software. When bubbles are detected (i.e. a peak in the filtered signal is found), the output is displayed in the user interface and the bubble count goes up. Furthermore, a time-based graph shows a running display of the amount of bubbles detected over a set period of time and updates continuously. The software also allows the signals to be recorded.

Figure 9A:
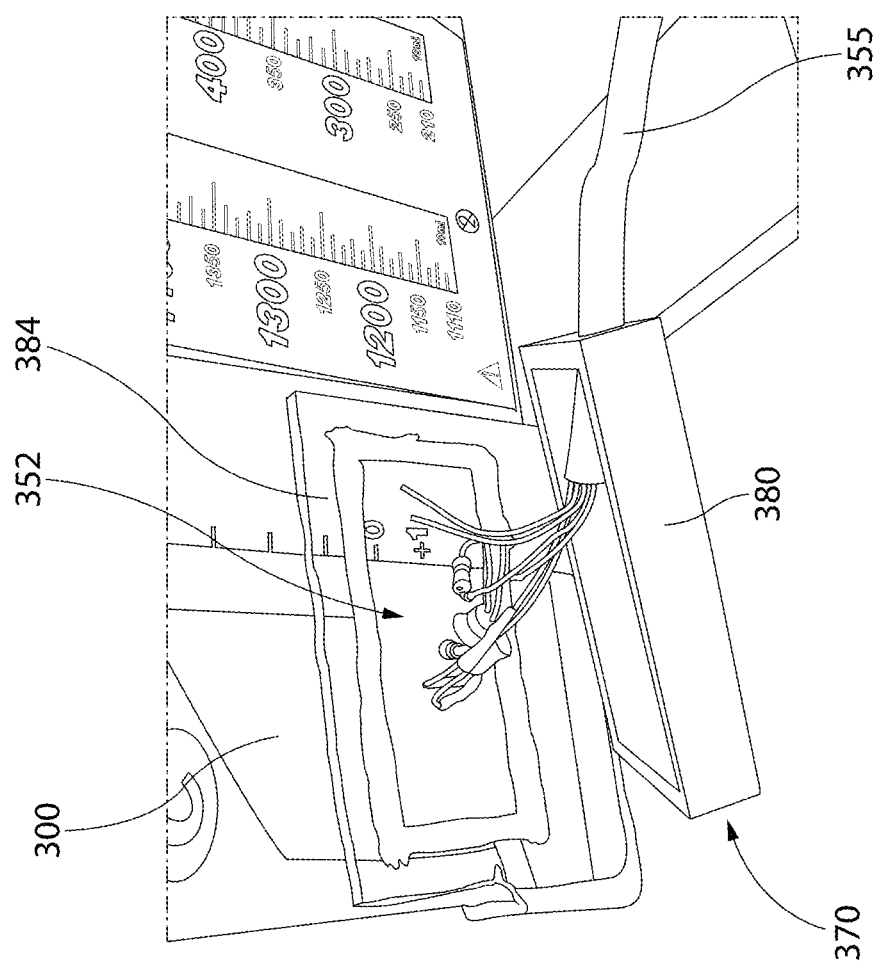
FIGS. 9A-9D are images of an experimental setup of a clip attached to a chest drainage system according to one embodiment.
Figure 9B:
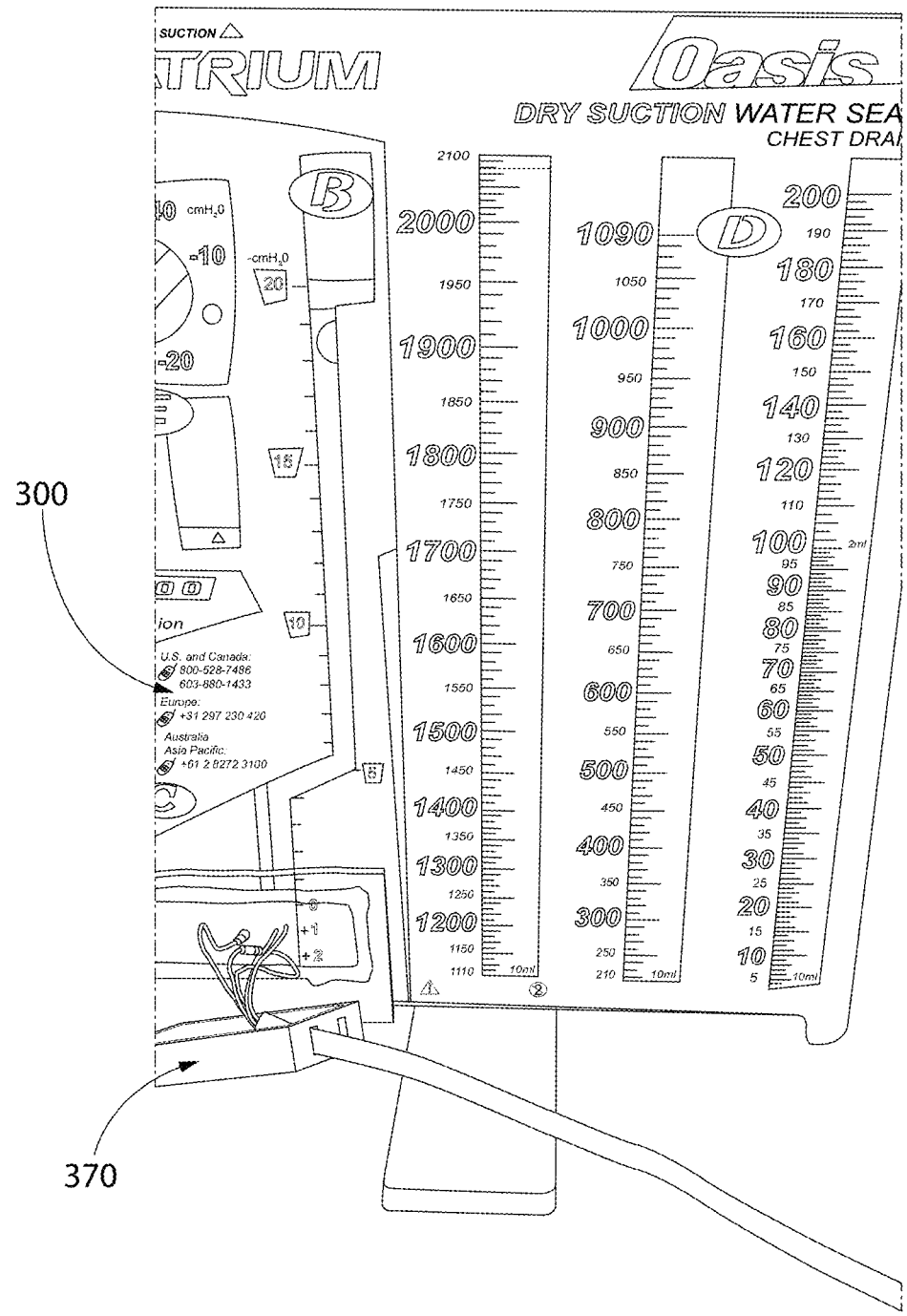
Figure 9C:
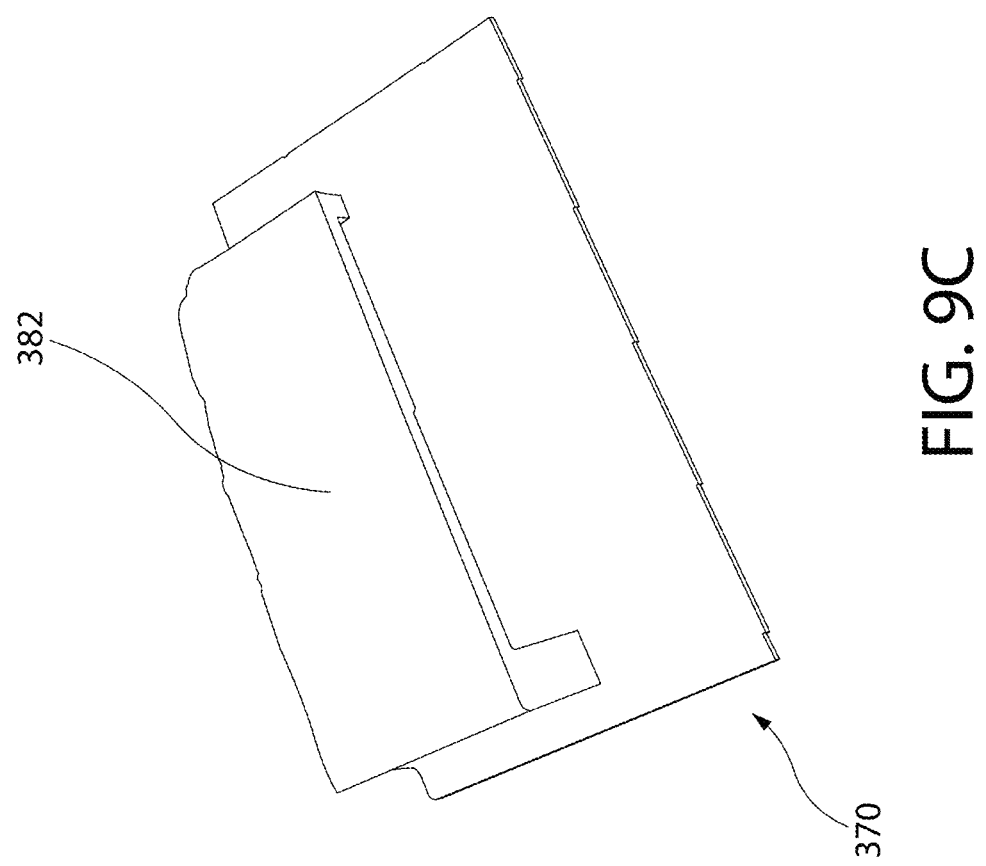
Figure 9D:
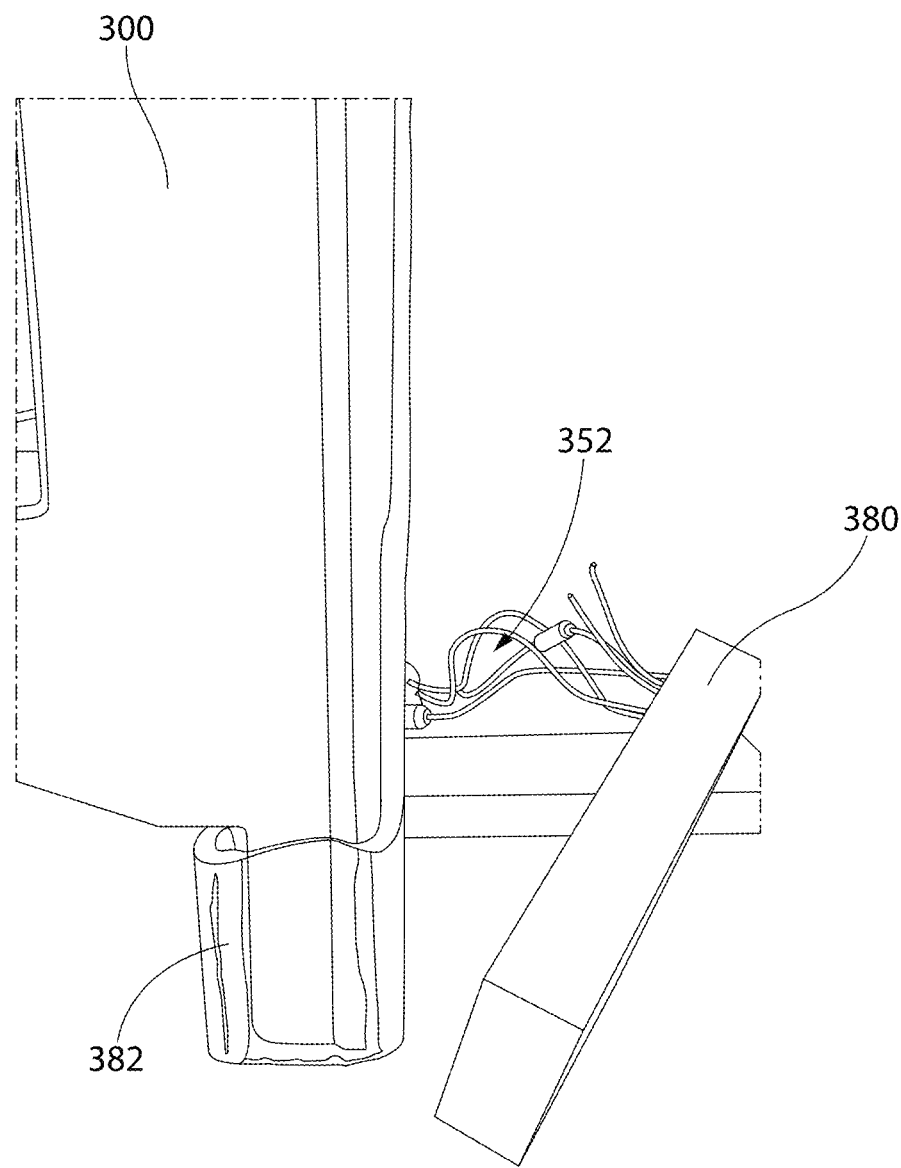

An experimental setup of a slide-on clip 370 and a chest drainage system 300 is shown in FIGS. 9A-9D, according to one embodiment. With reference first to FIGS. 9A and 9B, the housing 370 is plastic with certain portions being a transparent plastic 384 to allow for transmission of light. A photodetector and LED transmitter pair 352 are positioned within the housing 380 behind the transparent plastic. The detection elements are connected to a hardwire 355 for communication with a control module. The clip 370 is designed to be positioned over the water seal chamber window on the chest drainage system so that the photodetector and LED transmitter pair 352 are properly positioned for monitoring bubble activity. The back arm 382 of the clip 370 (shown magnified in FIG. 9C) has a geometry designed to wrap snug around the side of the chest drainage system 300 (shown magnified in FIG. 9D), keeping the clip secure.

The geometry of the clip can be modified or adjustable to fit the various models of chest drainage systems from different manufactures.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A chest tube drainage system comprising:
   a chest tube collection system comprising a drainage collection chamber, a water seal chamber having front and back surfaces, a suction control chamber, and a water seal tube in fluid communication with the drainage collection chamber and the water seal chamber; and
   a detachable air leak detection system;
   wherein the detachable air leak detection system comprises:
      a securement device having a first arm and an opposing second arm;
      a light emitting element disposed only on the first arm;
      a first photodetector disposed on the first arm adjacent to the light emitting element; and
      a second photodetector disposed on the second arm across from the light emitting element;
   wherein when the first and second arms of the securement device are attached to the front and back surfaces of the water seal chamber, the first photodetector is configured to detect reflected light emission generated by the light emitting element, and the second photodetector is configured to detect an interruption or refraction of light emission generated by the light emitting element.

2. The chest tube drainage system of claim 1, wherein the reflected light emission is reflected off of a fluid in the water seal chamber.

3. The chest tube drainage system of claim 1, wherein the reflected light emission is reflected off of one or more bubbles in the water seal chamber.

4. The chest tube drainage system of claim 1, wherein the light emitting element is an LED.

5. The chest tube drainage system of claim 1, wherein the light emitting element is disposed closer to the bottom portion of the water seal chamber than the first photodetector when the securement device is attached to the water seal chamber.

6. The chest tube drainage system of claim 1, wherein the first photodetector is disposed closer to a bottom of the water seal chamber than the light emitting element when the securement device is attached to the water seal chamber.

7. The chest tube drainage system of claim 1, wherein the securement device comprises at least one of a clip and an adhesive.

8. The chest tube drainage system of claim 1, wherein the securement device is transparent.

9. The chest tube drainage system of claim 1, wherein the air leak detection system is configured to perform a fast Fourier transform on the detected signal from at least one of the first and second photodetectors for determining when there is an air leak.

10. The chest tube drainage system of claim 1, wherein the air leak detection system comprises high and low bandpass filters to pass frequencies of 20-30 HZ and 70-90 Hz.

11. An air leak detection system comprising:
   a securement device having a first arm and an opposing second arm, wherein the first and second arms are configured to releasably attach to front and back surfaces of a water seal chamber of a chest tube collection system;
   a light emitting element disposed only on the first arm;
   a first photodetector disposed on the first arm and adjacent to the light emitting element; and
   a second photodetector disposed on the second arm and across from the light emitting element;
   wherein the first photodetector is configured to detect light emission reflected off of bubbles within the water seal chamber of the chest tube collection system in a same-side light detection mode, and the second photodetector is configured to detect an interruption or refraction of light emission in an opposite-side light detection mode.

12. The air leak detection system of claim 11, wherein the securement device is transparent.

13. The air leak detection system of claim 11, wherein the securement device comprises at least one of an adhesive and a clip.

14. The air leak detection system of claim 11, wherein the light emitting element is an LED.

15. The air leak detection system of claim 11, wherein the light emitting element and the first photodetector are disposed on the first arm of the securement device so that when the securement device is attached to the water seal chamber of the chest tube collection system, the light emitting element is positioned closer to a bottom portion of the water seal chamber of the chest tube collection system than the first photodetector.

16. The air leak detection system of claim 11, wherein the light emitting element and the first photodetector are disposed on the first arm of the securement device so that when the securement device is attached to the water seal chamber of the chest tube collection system, the first photodetector is positioned closer to a bottom of the water seal chamber of the chest tube collection system than the light emitting element.

17. The air leak detection system of claim 11 further comprising:
   high and low bandpass filters to pass frequencies of 20-30 HZ and 70-90 Hz.

18. The air leak detection system of claim 11 further comprising:
   an alert module configured to send a signal when a plurality of detected bubble events corresponding to the detected light emission reaches a threshold.

19. A method of detecting an air leak in a chest tube collection system comprising:
   attaching the securement device of claim 11 to front and back surfaces of a water seal chamber of a chest tube collection system;
   emitting light from the light emitting element towards bubbles generated by air leaving a water seal tube connecting a drainage collection chamber to the water seal chamber of the chest tube collection system; and
   detecting at least one of a reflection of the light using the first photodetector in a same-side light detection mode, and detecting an interruption or refraction of light using the second photodetector in an opposite-side light detection mode.

20. The method of claim 19, further comprising positioning the light emitting element closer to the bottom portion of the water seal chamber than the first photodetector.

21. The method of claim 19, further comprising positioning the first photodetector closer to a bottom of the water seal chamber than the light emitting element.

22. The method of claim 19, further comprising detecting a bubble event corresponding to a threshold frequency rise in the 20-30 HZ and 70-90 Hz ranges.

23. The method of claim 19, further comprising detecting a plurality of bubble events.

24. The method of claim 23, signaling an alert when the plurality of bubble events reaches a threshold.

* * * * *